United States Patent [19]

Farley

[11] Patent Number: 4,911,150
[45] Date of Patent: Mar. 27, 1990

[54] APPARATUS FOR TREATMENT OF INJURIES IN AN EQUINE LOWER LEG

[75] Inventor: Michael D. Farley, Burkittsville, Md.

[73] Assignee: Farley's Orthotics Inc., Melbourne, Fla.

[21] Appl. No.: 182,192

[22] Filed: Apr. 15, 1988

[51] Int. Cl.$^4$ .......................... A61F 3/00; A61F 5/04; B68C 5/00; A01K 29/00

[52] U.S. Cl. .............................. 128/80 R; 128/87 R; 54/82; 119/96

[58] Field of Search ................ 128/80 R, 80 C, 80 G, 128/80 A, 87 R, 80 H; 119/96, 108, 127, 143; 54/82

[56] References Cited

U.S. PATENT DOCUMENTS

| | | | |
|---|---|---|---|
| 739,634 | 9/1903 | Allen | 128/87 R |
| 1,070,869 | 8/1913 | Alexander | 128/87 R |
| 1,163,952 | 12/1915 | Richardson | 54/82 |
| 2,753,864 | 7/1956 | Weidemann, Jr. | 128/87 R |
| 3,232,289 | 2/1966 | Zimmerman | 128/87 R |
| 3,976,062 | 8/1976 | Cox | 128/87 R |
| 4,140,116 | 2/1979 | Hampicke | 54/82 |
| 4,361,143 | 11/1982 | Nelson | 128/87 R |
| 4,385,592 | 5/1983 | Goldstein | 119/96 |
| 4,424,809 | 1/1984 | Yovankin | 54/82 |
| 4,577,591 | 3/1986 | Wesseldine | 119/143 |

Primary Examiner—Robert A. Hafer
Assistant Examiner—Michael Brown
Attorney, Agent, or Firm—Berman, Aisenberg & Platt

[57] ABSTRACT

A boot for a foreleg of a horse is used in the treatment of injuries in the horse's leg. The boot includes an envelope of leather which is wrapped about the leg and secured by straps. The envelope has a flap which forms a pocket for receiving a strengthening spline. A variety of splines are provided to allow various stiffnesses to be used in the treatment of the injury.

6 Claims, 2 Drawing Sheets

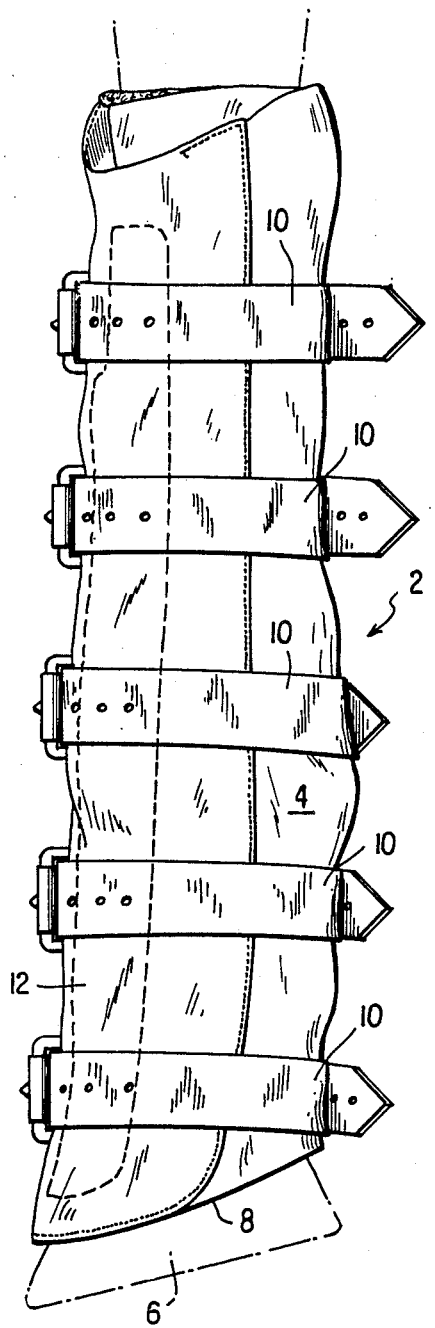
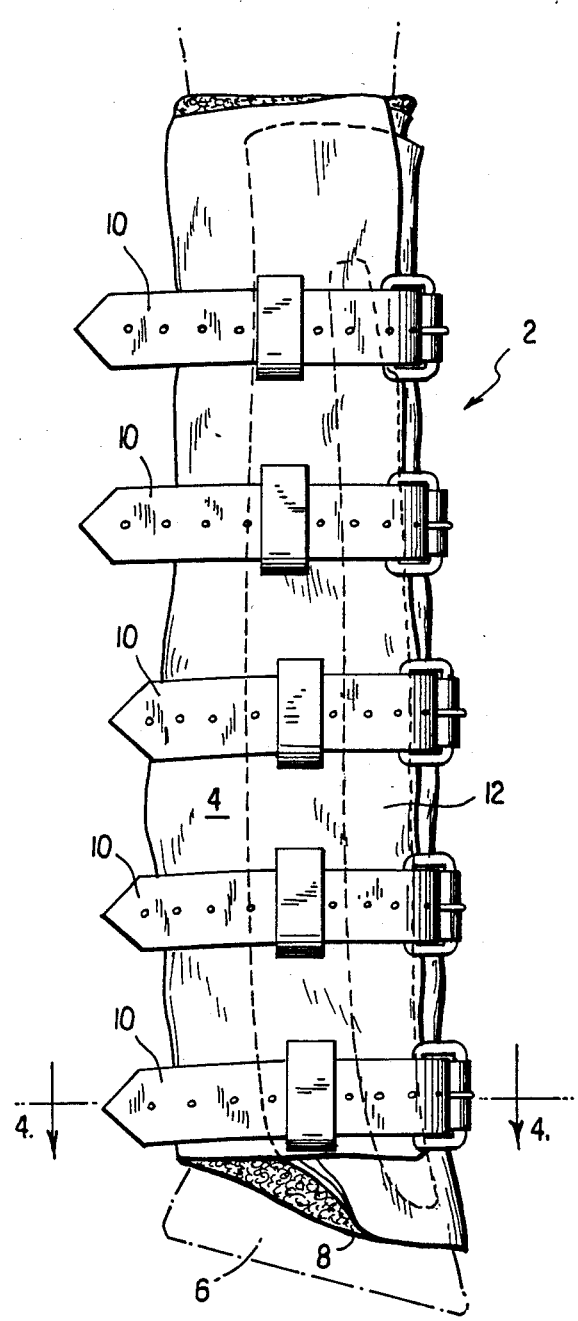
FIG. 1
FIG. 2

APPARATUS FOR TREATMENT OF INJURIES IN AN EQUINE LOWER LEG

TECHNICAL FIELD

This invention relates to the art of veterinary medicine. In particular the invention relates to a brace for use in treatment of injuries in the lower leg of a horse.

BACKGROUND ART

A horse's leg may be injured, such as by fractures or the like, and it is generally desirable to treat such legs. Treatment of an injured leg generally includes providing support to the joints involved until the injury can heal. Treatments in the past have relied on the use of a plaster cast to immobilize the affected joint during the period of treatment. This treatment has not proven satisfactory because the horse considers the cast to be a foreign object which it tries to remove, causing further injury. Moreover, the cast prevents any motion of the joint and does not allow it to gain strength during the period of treatment.

Other known treatments include the application of a support in the form of a wrapping of tape, or the like. This method suffers from several disadvantages. For example, the tape is often unable to provide the substantial amount of support required for treatment of serious injuries, and the required repeated application of the tape is difficult and time consuming.

SUMMARY OF THE INVENTION

In accordance with the invention, an apparatus is provided which is easily attached to the lower part of a horse's leg for treatment of injuries in and around the ankle joint. The apparatus preferably comprises a boot which fits around the lower part of the leg and extends from a point just below the knee to a point near the bottom of the hoof wall. The boot has a pocket therein which extends along the entire length of the front of the boot for receiving one of a plurality of strengthening splines. The splines are removable so that they may be changed as the treatment proceeds. For example, in a typical treatment, a stiff spline is used in the initial stage of treatment of an injury. The stiff spline limits the motion of the joint to a large extent and transfers most of the weight of the horse to its canon bone and hoof wall. As the treatment progresses, the stiff spline is replaced with a succession of splines of lesser stiffness to permit a greater motion of the joint and gradually to require the ligaments and joints to carry more weight. By this technique, the joint is caused to regain its strength gradually, and the horse is permitted freedom to move about earlier, thus increasing the effectiveness of the treatment.

As will be made more clear from the detailed description of the preferred embodiment, the inventive apparatus is designed to relieve stress on the check ligament, suspensory ligament, and flexor tendon by distributing the weight of the animal to the front of the hoof wall, the front of the ankle, and the front of the canon bone. By substituting inserts of varying stiffness, the degree of weight distributed can be varied from nearly one hundred percent to a small percentage.

In the preferred embodiment the apparatus is a leather boot comprising a leather envelope adapted to be wrapped around the lower leg and secured by five straps. A pocket lies along the front of the envelope for receiving molded plastic polymer replaceable splines, and the pocket is between the envelope and the straps. The leather envelope is lined with sheepskin to minimize development of pressure sores.

It is an object of this invention to provide a novel apparatus for the treatment of injuries in an equine leg.

Another object of this invention is to provide an apparatus for treatment of an injury in the leg of a horse wherein the movement of the joint may be adjusted.

Yet another object of this invention is to provide an apparatus for treatment of an injury of a leg wherein a selected one of a plurality of stiffening splines may be inserted into a pocket.

BRIEF DESCRIPTION OF THE DRAWINGS

FIG. 1 is a side view of an apparatus in accordance with the invention showing a horse's right foreleg in phantom lines.

FIG. 2 is a side view similar to that of FIG. 1 from an opposite side.

DETAILED DESCRIPTION OF THE PREFERRED EMBODIMENT

Figure 3:
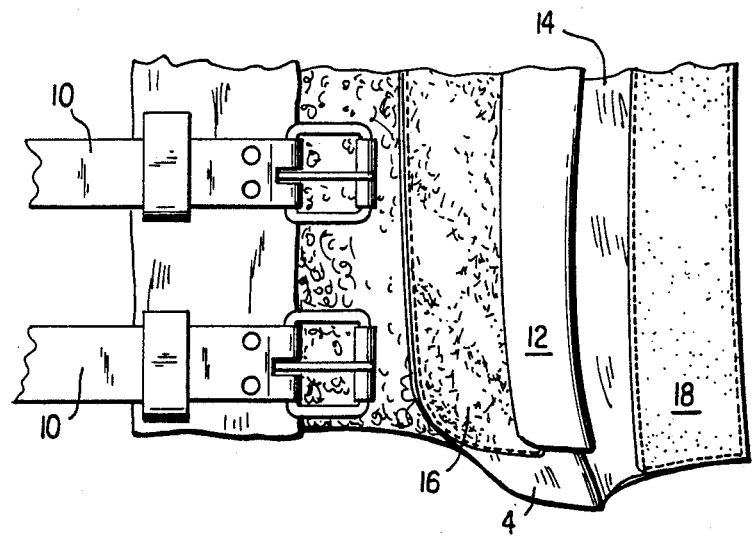
FIG. 3 is a side view of a lower portion of an opened apparatus in accordance with the invention.

With reference to FIGS. 1 and 2, a boot 2 for the right leg of a horse comprises a leather envelope 4 which extends from near the bottom of the wall of a hoof 6 of a foreleg of a horse to a location just below the knee. The envelope 4 has a lower edge 8 which engages the hoof and, along with the portion of the interior of the envelope which also engages the hoof wall, transfers downwardly-directed force on the envelope 4 to the hoof 6.

Envelope 4 is applied to the foreleg of the horse by wrapping it about the foreleg and securing it by straps 10. The buckles of the straps are preferably located on the outside of the horse's leg when the boot is installed. Thus, there are preferably a right and a left boot.

A spline 12 is encased within a pocket in envelope 4, the pocket being located on the front of the envelope, for providing adjustable stiffness to the boot. A series of splines 12 of various stiffnesses is preferably supplied with the boot. A selected spline which is somewhat stiff may be used for a newly injured leg, and splines of lesser stiffness may be used as the injury heals. This permits a maximum level of support initially for the injured foreleg and a reduction in the support as the foreleg strengthens.

FIG. 3 is a view of a lower part of boot 2 in an unfolded condition showing the pocket opened. Envelope 4 includes a flap 14 which extends along the entire front of the boot and forms the pocket for receiving spline 12. Envelope 4 has a strip 16 of Velcro material which cooperates with a strip 18 of Velcro material on an inner face of flap 14. The cooperation between strips 16 and 18 allows the pocket created between envelope 4 and flap 14 to be readily opened to allow insertion of spline 12 and closed to secure spline 12 in the pocket.

Figure 4:
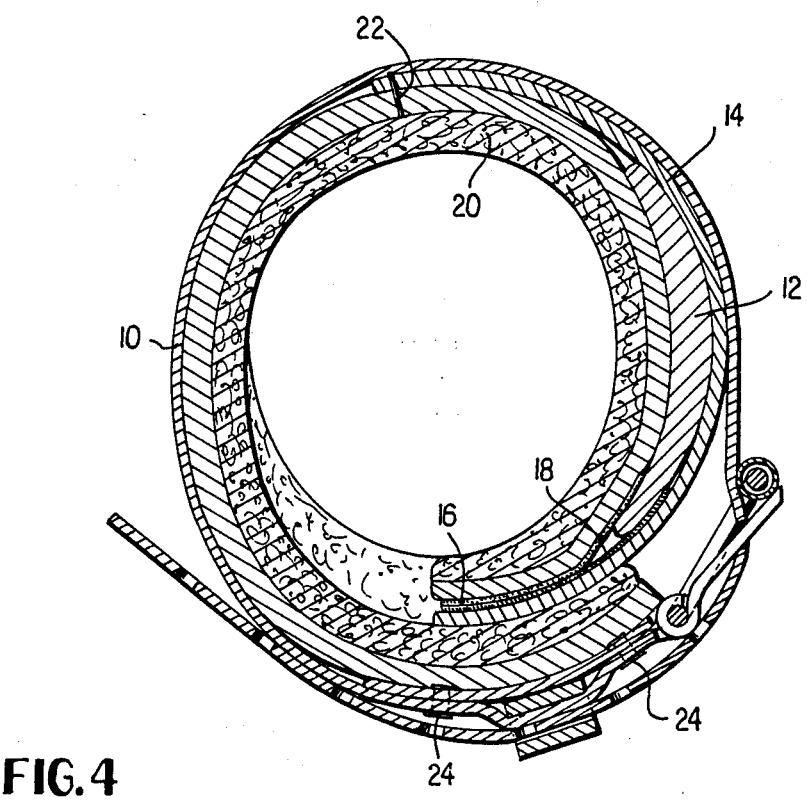
FIG. 4 is a cross section taken along line 4—4 of FIG. 2.

FIG. 4 is a cross-section taken along line 4—4 of FIG. 2 and shows the preferred construction of the boot in more detail. The flap 14 is held tightly between overlapped ends of envelope 4, and this overlapping along with the action of straps 10 operates to securely retain the spline in its pocket. This prevents movement of spline 12 with respect to envelope 4 and results in a rugged structure. It will be appreciated that, while flap 14 is shown secured to envelope 4 by stitches 22 and straps 10 are shown secured by rivets 24, many other constructions are possible.

Spline 12 is preferably molded to conform generally to the shape of the foreleg of the horse and the upper part of its hoof wall. Thus, spline 12 is somewhat cylindrical and provides a slightly enlarged concave portion at a location generally adjacent the ankle. The spline also curves forwardly at its lower portion, in the region adjacent the hoof wall (see FIGS. 1 and 2), to assist in the transfer of forces on the spline to the hoof. A much thinner part 26 (see FIG. 1) is located at the top of the spline just below the knee.

The inner surface of leather envelope 4 is preferably covered with a layer of foam and sheepskin 20 to reduce abrasion between envelope 4 and the horse's leg.

It will be appreciated that a unique boot forming a pocket for receiving one of a plurality of splines and a method for use thereof have been described. Modifications within the scope of the appended claims will be apparent to those of skill in the art.

I claim:

1. Apparatus for treatment of injuries in a leg of an animal, said leg having a knee and a hoof, comprising envelope means for surrounding a lower part of said leg and extending from just below said knee to the wall of said hoof, a pocket attached to the front of said envelope and extending substantially the entire length of said envelope, and spline means in said pocket for stiffening said envelope means and for engaging said hoof wall for transferring the weight of said animal to the front of said hoof wall.

2. Apparatus according to claim 1 further comprising a plurality of spaced straps for securing said envelope means to said leg.

3. Apparatus according to claim 2 wherein said pocket is formed between a first portion of said envelope which is adapted to engage said leg and a flap attached to said envelope and wherein said flap is between said straps and said first portion.

4. Apparatus according to claim 1 wherein said spline means comprises a plurality of individual splines, each of said individual splines having a different stiffness.

5. Apparatus according to claim 1 wherein a lower end of said spline curves forwardly.

6. A method for treatment of injuries in the leg of a horse comprising attaching an apparatus to the foreleg of said horse, said apparatus comprising envelope means surrounding a lower part of said leg and extending from just below a knee of said leg to the wall of a hoof of said leg, a pocket attached to the front of said envelope and extending substantially the entire length of said envelope, and a first spline in said pocket for stiffening said envelope and engaging said hoof wall for transferring the weight of said horse to the front wall of said hoof, and subsequently removing said first spline and substituting a second spline therefor, said second spline being lesser stiffness than said first spline.

* * * * *